United States Patent [19]

Buckle et al.

[11] 4,031,099

[45] June 21, 1977

[54] 4-HYDROXY-3-NITRO-5,6,7,8 TETRAHYDRO-CARBOSTYRILS

[75] Inventors: Derek Richard Buckle, Redhill; Barrie Christian Charles Cantello, Horsham; Harry Smith, Maplehurst, all of England

[73] Assignee: Beecham Group Limited, England

[22] Filed: Oct. 7, 1974

[21] Appl. No.: 512,949

[30] Foreign Application Priority Data

Oct. 11, 1973 United Kingdom ............ 47508/73

[52] U.S. Cl. .................. 260/289 K; 260/287 H; 260/270 Q; 260/288 R; 260/295 K; 260/296 B; 260/297 B; 424/258

[51] Int. Cl.² ............... C01D 215/18; A61K 31/47
[58] Field of Search ................... 260/289 K, 270 Q

[56] References Cited

FOREIGN PATENTS OR APPLICATIONS

| 205,502 | 3/1959 | Austria | 260/289 K |
| 2,009,119 | 1/1970 | France | 260/289 K |
| 1,369,634 | 9/1963 | France | 260/289 K |

*Primary Examiner*—Donald G. Daus
*Assistant Examiner*—D. B. Springer

[57] ABSTRACT

A class of 4-hydroxy-3-nitro-α-pyridones have antiallergic activity.

5 Claims, No Drawings

4-HYDROXY-3-NITRO-5,6,7,8 TETRAHYDRO-CARBOSTYRILS

This invention relates to pharmaceutical compositions which are useful in the inhibition of the effects of certain types of antigen - antibody reaction and are therefore of value in the prophylaxis and treatment of diseases associated with allergic or immunological reactions, e.g. certain types of asthma and hay-fever and also in the treatment of rhinitis.

In our British Application Nos. 24317/73 and 24000/73, which matured into British Pat. No. 1,453,863, issued Oct. 27, 1976, and which papers are contained in U.S. Pat. No. 3,962,445 we have described and claimed a pharmaceutical composition comprising a compound of formula (I) or a pharmaceutically acceptable salt thereof:

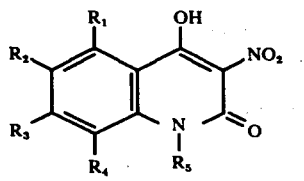

together with one or more pharmaceutically acceptable carriers, in which formula $R_1$, $R_2$, $R_3$ and $R_4$ represent hydrogen or alkyl, alkoxy, aryloxy, aralkoxy, aryl, aralkyl, heterocyclic, hydroxy, nitro, amino, acylamino or halogen groups or any two of the groups $R_1$, $R_2$, $R_3$ and $R_4$ may be joined in a carbocyclic or heterocyclic ring system, and $R_5$ represents hydrogen or an alkyl, aryl or aralkyl group.

These compositions and compounds have useful activity in mammals in that they inhibit the effects of certain types of antigen - antibody reactions.

The present invention is an improvement in or a modification of the invention described above, in that we have found that a class of 3-nitro-α-pyridones of the formula (II):

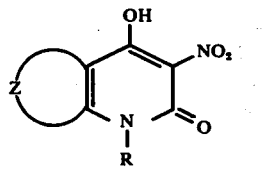

wherein R is hydrogen or an alkyl, aryl, or aralkyl group and Z represents the residue of a cyclooctyl, cycloheptyl, cyclohexyl or cyclopentyl ring, any of which residues may carry substituents, are also active in mammals in inhibiting the effects of certain types of antigen - antibody reactions. However, a search of the chemical literature has revealed that some of the members of the class (II) are known compounds, for example:

2,4-dihydroxy-3-nitro-5,6,7,8-tetrahydroquinoline,
2,4-dihydroxy-3-nitro-8-methyl-5,6,7,8-tetrahydroquinoline,
2,4-dihydroxy-3-nitro-6-methyl-5,6,7,8-tetrahydroquinoline,
5,6-cyclopenteno-2,4-dihydroxy-3-nitropyridine and derivatives thereof. (French Pat. No. 1,369,634; 1963).

Although these compounds have been reported in the literature, no form of useful biological activity have been ascribed to them. Likewise there has been in the literature no suggestion that such compounds are likely to possess any form of useful biological activity and in particular the discovery that they have anti-allergic activity has not been predicted in any way.

Accordingly the present invention provides a pharmaceutical composition comprising a compound of formula (II):

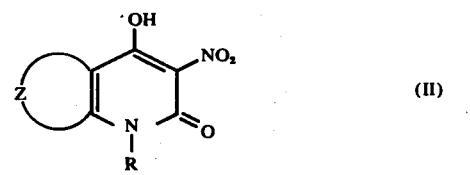

or a pharmaceutically acceptable salt thereof, wherein R is hydrogen or an alkyl, or aralkyl group and Z represents the residue of a cyclooctyl, cycloheptyl, a cyclohexyl or a cyclopentyl ring, any of which residues may carry substituents selected from alkyl, alkoxy, aryloxy, aralkoxy, aryl, aralkyl, heterocyclic, hydroxy, nitro, amino, acylamino or halogen groups or any two substituents taken together may represent the residue of a substituted or unsubstituted carbocyclic or heterocyclic ring system; together with one or more pharmaceutically acceptable carriers.

Examples of compounds of formula (II) wherein Z is the residue of a cyclooctyl ring are compounds of the formula (III):

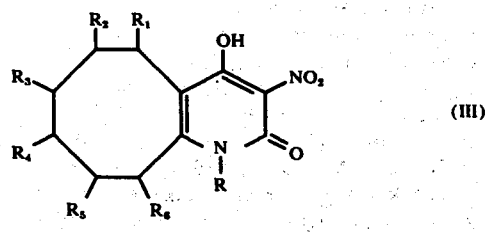

or pharmaceutically acceptable salts thereof.

Examples of compounds of formula (II) wherein Z is the residue of a cycloheptyl ring are compounds of the formula (IV):

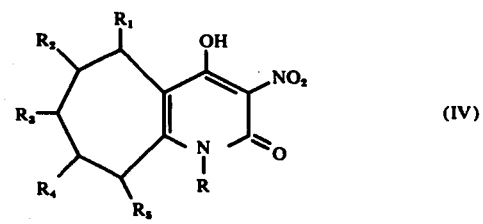

or pharmaceutically acceptable salts thereof.

Examples of compounds of formula (II) wherein Z is the residue of a cyclohexyl ring are compounds of the formula (V):

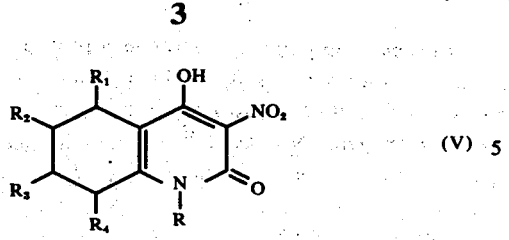

(V)

or pharmaceutically acceptable salts thereof.

Examples of compounds of formula (II) wherein Z is the residue of a cyclopentyl ring are compounds of the formula (VI):

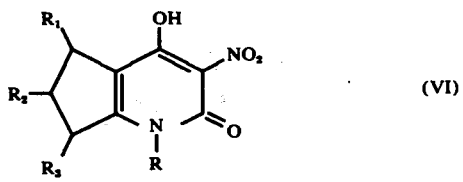

(VI)

or pharmaceutically acceptable salts thereof.

The substituents $R_1$, $R_2$, $R_3$, $R_4$, $R_5$ and $R_6$ in formula (III), $R_1$, $R_2$, $R_3$, $R_4$ and $R_5$ l in formula (IV), $R_1$, $R_2$, $R_3$ and $R_4$ in formula (V) and $R_1$, $R_2$ and $R_3$ in formula (VI) are each hydrogen or alkyl, alkoxy, aryloxy, aralkoxy, aryl, aralkyl, heterocyclic, hydroxy, nitro, amino, acylamino or halogen groups. In addition, any two of the groups $R_1$, $R_2$, $R_3$, $R_4$, $R_5$ and $R_6$ in formula (III), $R_1$, $R_2$, $R_3$, $R_4$ and $R_5$ in formula (IV), $R_1$, $R_2$, $R_3$ and $R_4$ in formula (V) and $R_1$, $R_2$ and $R_3$ in formula (VI) taken together may represent the residue of a substituted or unsubstituted carbocyclic or heterocyclic ring system.

Examples of the groups $R_1$, $R_2$, $R_3$, $R_4$, $R_5$ and $R_6$ in formula (III), $R_1$, $R_2$, $R_3$, $R_4$ and $R_5$ in formula (IV), $R_1$, $R_2$, $R_3$ and $R_4$ in formula (V) and $R_1$, $R_2$ and $R_3$ in formula (VI) which may be present are methyl, ethyl, n- and iso-propyl, n-, sec- and tert-butyl, methoxy, ethoxy, n-, and iso-propoxy, n-, sec- and tert-butoxy, phenoxy, benzyloxy, phenyl, benzyl, pyridyl, fluoro, chloro, bromo, iodo, or acetamido. In addition $R_1$ and $R_2$, $R_2$ and $R_3$, $R_3$ and $R_4$, $R_4$ and $R_5$ l or R5 and $R_6$ in formula (III), $R_1$ and $R_2$, $R_2$ and $R_3$, $R_3$ and $R_4$ or $R_4$ and $R_5$ in formula (IV), $R_1$ and $R_2$, $R_2$ and $R_3$ or $R_3$ and $R_4$ in formula (V) and $R_1$ and $R_2$ or $R_2$ and $R_3$ in formula (VI) taken together may represent the residue of a 1, 2-phenylene ring or a 1, 2-cyclohexenylene ring which may carry one or more of the substituents listed above.

A subclass of compounds which may be incorporated into the compositions of this invention are those of formula (II) wherein R is hydrogen or lower alkyl and the substituents on the residue Z are hydrogen or lower alkyl.

Compounds of formula (II) wherein Z is the residue of a cyclohexyl ring, which may carry one or more of the substituents listed above, i.e. compounds of formula (V), or pharmaceutically acceptable salts thereof, are preferred for their generally higher level of activity. Within this class, preferred compounds are those of formula (V) wherein R and $R_4$ are hydrogen and one or two of $R_1$, $R_2$ and $R_3$ are lower alkyl. Preferably $R_2$ is hydrogen.

Examples of suitable salts of compounds of formula (II) include the alkali metal salts, particularly potassium and sodium, and the alkaline earth metal salts such as aluminium and magnesium salts, as well as salts with organic bases such as amines or amino compounds.

Individual compounds which may be included in the compositions of this invention include the following:

4-hydroxy-3-nitro-5,6,7,8-tetrahydrocarbostyril;
4-hydroxy-7-methyl-3-nitro-5,6,7,8-tetrahydrocarbostyril;
5,6-cyclopenteno-4-hydroxy-3-nitro-α-pyridone;
5,6-cycloheptenyl-4-hydroxy-3-nitro-α-pyridone;
5,7-dimethyl-4-hydroxy-3-nitro-5,6,7,8-tetrahydrocarbostyril;
4-hydroxy-6-methyl-3-nitro-5,6,7,8-tetrahydrocarbostyril;
5,6-cyclooctenyl-4-hydroxy-3-nitro-α-pyridone;
1-ethyl-4-hydroxy-3-nitro-5,6,7,8-tetrahydrocarbostyril;
4-hydroxy-3-nitro-1-n-propyl-5,6,7,8-tetrahydrocarbostyril;
4-hydroxy-1-isopropyl-3-nitro-5,6,7,8-tetrahydrocarbostyril;
1-ethyl-4-hydroxy-7-methyl-3-nitro-5,6,7,8-tetrahydrocarbostyril;
7-ethyl-4-hydroxy-3-nitro-5,6,7,8-tetrahydrocarbostyril;
6,7-diethyl-4-hydroxy-3-nitro-5,6,7,8-tetrahydrocarbostyril;
6,7-dimethyl-4-hydroxy-3-nitro-5,6,7,8-tetrahydrocarbostyril.

Substituted 4-hydroxy-3-nitro-α-pyridones may exist in a number of tautomeric forms:

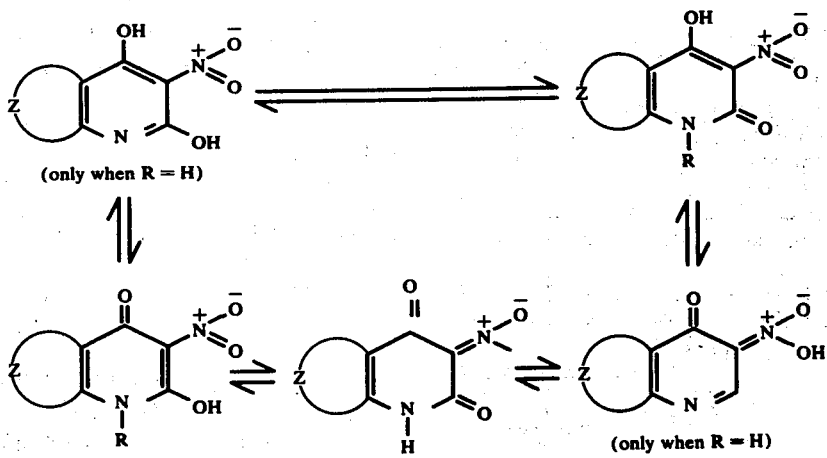

and it is to be understood that in this specification reference to substituted 4-hydroxy-3-nitro-α-pyridones also includes tautomeric forms of these compounds.

The composition of this invention may be presented as a micro fine powder for insufflation, e.g. as a snuff or in capsules of hard gelatine. They may also be presented with a sterile liquid carrier for injection. Compounds of formula (II) which are active when given by the oral route, may be compounded in the form of syrups, tablets, capsules, pills and the like. Preferably the compositions are in unit dosage form, or in a form in which the patient can administer to himself a single dosage. If desired, a small amount of bronchodilator compound such as isoprenaline may be incorporated into the compositions of this invention both to inhibit the cough response if the composition is insufflated and to provide immediate relief during an asthmatic attack. The effective dose of compound (II) depends on the particular compound employed, but is in general in the range of from 0.1 mg/kg/day to 100 mg/kg/day.

The precise nature of the pharmaceutical carrier used in the composition of this invention is not important. Standard pharmaceutical practice may be followed but it is perhaps worth noting that if the composition is to be administered by insufflation, a microfine powder wherein substantially all the particles have diameters of less than 50 microns is preferred.

As is common practice, the compositions will usually be accompanied by written or printed directions for use in the medical treatment concerned, in this case as an anti-allergic agent for prophylaxis of, for example, asthma, hay-fever or rhinitis.

Most of the compounds defined above with respect to formula (II) are novel compounds, although some of the compounds falling within the scope of formula (II) are disclosed in French Pat. No. 1,369,634. However, that patent does not indicate in any way the anti-allergic activity of the compounds.

Accordingly the present invention also includes within its scope compounds of formula (II) and pharmaceutically acceptable salts thereof, provided that when R is hydrogen, the moeity Z is not an unsubstitutued residue of a cyclopentyl or cyclohexyl ring or a 6-methyl or 8-methyl substituted residue or a cyclohexyl ring.

With that proviso, preferred sub-classes of novel compounds are as defined above with reference to the compositions.

A preferred class of novel compounds of this invention are those of formula (VA) and pharmaceutically acceptable salts thereof:

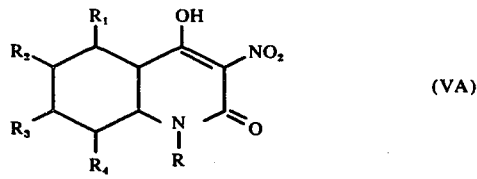

(VA)

wherein R, $R_1$, $R_2$, $R_3$ and $R_4$ are as defined with respect to formula (V), provided that a. $R_2$ is not hydrogen or methyl when R, $R_1$, $R_3$ and $R_4$ are each hydrogen; and b. $R_4$ is not methyl when R, $R_1$, $R_2$ and $R_3$ are each hydrogen.

In a preferred sub-class, R, $R_2$ and $R_4$ are hydrogen and one or both of $R_1$ and $R_3$ is lower alkyl and the other is hydrogen.

In another preferred sub-class, R, $R_1$ and $R_4$ are hydrogen and one or both of $R_2$ and $R_3$ are lower alkyl and the other is hydrogen provided that, when $R_3$ is hydrogen, $R_4$ is not hydrogen or methyl.

Specific compounds of formula (VA) which are preferred include the following and their pharmaceutically acceptable salts:

4-hydroxy-7-methyl-3-nitro-5,6,7,8-tetrohydrocarbostyril;

5,7-dimethyl-4-hydroxy-3-nitro-5,6,7,8-tetrahydrocarbostyril;

7-ethyl-4-hydroxy-3-nitro-5,6,7,8-tetrohydrocarbostyril;

6,7-diethyl-4-hydroxy-3-nitro-5,6,7,8-tetrahydrocarbostyril;

6,7-dimethyl-4-hydroxy-3-nitro-5,6,7,8-tetrahydrocarbostyril.

Compounds of the formula (II) may be prepared by nitrating the parent 2,4-dihydroxypyridine (VII):

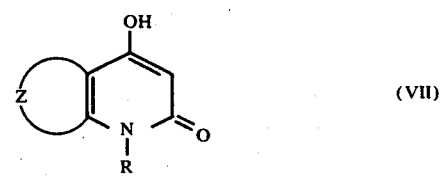

(VII)

wherein R and Z are as defined in formula (II). Nitration may be effected using one of the following nitrating agents:

i. the nitrous fumes generated with concentrated nitric acid and arsenic oxide;

ii. acetic acid plus concentrated nitric acid;

iii. fuming nitric acid in chloroform;

iv. concentrated nitric acid.

The preferred process is method (ii).

The starting materials of formula (VII) wherein R is other than H may be prepared by standard methods known from the literature. For example the method of Ziegler et. al. *Monatsch* 97, 1394, (1966) may be employed where an appropriately substituted compound of formula (VIII) is treated with a strong base such as sodium methoxide:

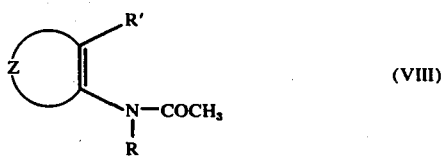

(VIII)

wherein Z is as defined with respect to formula (II), R is alkyl, aryl, or aralkyl, and R is a carboxylic ester group.

The compounds of formula (VII) wherein R is hydrogen may be prepared by essentially the method of V. Prelog and S. Szpilfogel (Helv. Chim. Acta. 28, 1684 (1945)), where an appropriately substituted enamine (IX):

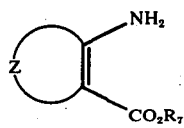

(IX)

wherein Z is as defined in formula (II) and $R_7$ is a methyl or ethyl group, is reacted with diethyl malonate to give a compound of formula (X):

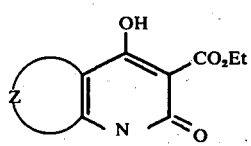

(X)

wherein Z is as defined in formula (II), followed by refluxing the compound of formula (X) with acid to give the corresponding α-pyridone VII.

The following examples illustrate the preparation and properties of some of the compounds of the invention:

EXAMPLE 1 a. 3-Carboethoxy-4-hydroxy-5,6,7,8-tetrahydrocarbostyril

A mixture of a 60:40 mixture of the ethyl and methyl esters of 2-amino cyclohex-1-ene carboxylic acid (47.2g; 0.29 mole) and diethyl malonate (46.4g; 0.29 mole) were added to a solution of sodium (7.2g; 0.29 mole) in ethanol (145 ml) stirred at ca 110° C for 30 hrs. in an autoclave. The product was acidified with 5N HCl to pH 4.0 and diluted with water. The precipitated ester was filtered off and recrystallised from ethanol with charcoalisation, m.p. 236° –7° (d).

(Found: C, 60.92; H, 6.41; N, 6.17; $C_{12}H_{15}NO_4$. Requires: C, 60.75; H, 6.37; N, 5.90%).

b. 4-Hydroxy-5,6,7,8-tetrahydrocarbostyril

A suspension of 3-carboethoxy-4-hydroxy-5,6,7,8-tetrahydro-carbostyril (19.4g; 0.082 mole) in 2N hydrochloric acid (200 ml) was refluxed 30 hrs. and the clear solution evaporated to dryness. Water was added and the solution brought to pH 4.0 with dilute sodium hydroxide solution. The precipitated white product was filtered off, washed well with water and recrystallised from glacial acetic acid, m.p. >330° C.

(Found: C, 65.25; H, 6.87; N, 8.33; $C_9H_{11}NO_2$. Requires: C, 65.44; H, 6.71; N, 8.48%).

c. 4-Hydroxy-3-nitro-5,6,7,8-tetrahydrocarbostyril

A solution of 4-hydroxy-5,6,7,8-tetrahydrocarbostyril (1.70g; 0.0103 mole) and concentrated nitric acid (2.5 ml; d 1.42), in glacial acetic acid (10 ml) was heated at 100° C till the oxides of nitrogen were evolved and rapidly cooled in ice. Water (40 ml) was added to the red solution to precipitate the yellow-orange 3-nitro derivative. After filtration, thorough washing with water and recrystallisation from acetic acid - ethanol the product had m.p. 241° (d).

(Found: C, 51.76; H, 4.99; N, 12.99; $C_9H_{10}N_2O_4$. Requires: C, 51.43; H, 4.80; N, 13.33%).

EXAMPLE 2 a. 3-Carboethoxy-4-hydroxy-7-methyl-5,6,7,8-tetrahydrocarbostyril

A mixture of the ethyl and methyl esters (9:1 ratio) of 2-amino-4-methyl cyclohex-1-ene carboxylic acid (48.0g; 0.264 mole) was treated as given in example 1a, to afford the title product, m.p. (EtOH) 247° –8° (d).

(Found: C, 62.44; H, 6.82; N, 5.42; $C_{13}H_{17}NO_4$. Requires: C, 62.14; H, 6.82; N, 5.57%).

b. 4-Hydroxy-7-methyl-5,6,7,8-tetrahydrocarbostyril

A suspension of 3-carboethoxy-4-hydroxy-7-methyl-5,6,7,8-tetrahydrocarbostyril (7.48 g; 0.03 mole) in 2N hydrochloric acid (50 ml) was refluxed 48 hrs. and the clear solution evaporated to dryness. After resolution in water and adjusting to pH 4.0 the precipitated white solid was filtered, washed well with water and recrystallised from acetic acid, m.p. >360°.

(Found: C, 66.67; H, 7.40; N, 7.61; $C_{10}H_{13}NO_2$. Requires: C, 67.02; H, 7.31; N, 7.82%).

c. 4-Hydroxy-7-methyl-3-nitro-5,6,7,8-tetrahydrocarbostyril

A suspension of 4-hydroxy-7-methyl-5,6,7,8-tetrahydrocarbostyril, (1.608 g; 0.009 mole) in glacial acetic acid (10 ml) was treated with concentrated nitric acid (2.5 ml; d 1.42) and the clear solution heated at 100° C until the exothermic reaction set in (ca 7 mins). After rapid cooling water (40 ml) was added and the yellow solid filtered off and recrystallised from ethanol; acetic acid, m.p. 238° (d).

(Found: C, 53.35; H, 5.41; N, 12.62; $C_{10}H_{12}N_2O_4$. Requires: C, 53.57; H, 5.39; N, 12.49%).

EXAMPLE 3 a. 3-Carboethoxy-5,6-cyclopenteno-4-hydroxy-α-pyridone

A mixture of the ethyl and methyl esters (1:1 ratio of 2-amino cyclopent-1-ene carboxylic acid (47.75 g; 0.322 mole) was treated with diethyl malonate as described in example 1a to yield the title product, m.p. (EtOH) 229° –233° (d).

(Found: C, 59.31; H, 5.84; N, 6.19; $C_{11}H_{13}NO_4$. Requires: C, 59.19; H, 5.87; N, 6.27%).

b. 5,6-Cyclopenteno-4-hydroxy-α-pyridone

A suspension of 3-carboethoxy-5,6-cyclopenteno-4-hydroxy-α-pyridone (24.58 g; 0.11 mole) in 2N hydrochloric acid (200 ml) was refluxed 24 hrs. and the cooled solution evaporated to dryness. After re-dissolution in water and adjusting the pH to 4.0 with dilute sodium hydroxide solution the white precipitate was filtered off, washed well with water and recrystallised from glacial acetic acid, m.p. 310° C.

(Found: C, 63.80; H, 6.06; N, 9.21; $C_8H_9NO_2$. Requires: C, 63.57; H, 6.00; N, 9.27%).

c. 5,6-Cyclopenteno-4-hydroxy-3-nitro-α-pyridone

A suspension of 5,6-cyclopenteno-4-hydroxy-α-pyridone (1.36 g; 0.009 mole) in glacial acetic acid (10 ml) was treated with concentrated nitric acid (2.5 ml; d 1.42) and the clear, colourless solution was heated at 100° C on a steam bath. As soon as the red colour appeared and nitrogen oxide evolution ensured the solution was rapidly cooled and diluted with water. The yellow precipitate was filtered off, washed well with water and recrystallised from acetic acid; ethanol, m.p. 243° (d).

(Found: C, 48.92; H, 4.06; N, 12.26; $C_8H_8N_2O_4$. Requires: C, 48.98; H, 4.11; N, 14.28%).

EXAMPLE 4 a. 3-Carboethoxy-5,6-cycloheptenyl-4-hydroxy-α-pyridone

A solution of ethyl 2-amino cyclohept-1-ene-1-carboxylate (40.8 g; 0.212 mole) and diethyl malonate (34.0 g; 0.212 mole) in ethanolic sodium ethoxide (5.25 g; Na in 105 ml. EtOH) was treated as described in example 1a. The product on recrystallisation from ethanol had, m.p. 213° –6° C.

(Found: C, 62.19; H, 6.86; N, 5.77; $C_{13}H_{17}NO_4$. Requires: C, 62.14; H, 6.82; N, 5.57%).

b. 5,6-Cycloheptenyl-4-hydroxy-α-pyridone

A suspension of 3-carboethoxy-5,6-cycloheptenyl-4-hydroxyα-pyridone (20.0g; 0.08 mole) in 2N hydrochloric acid (300 ml) was refluxed 48 hrs. and the clear solution evaporated to dryness. The white solid was suspended in water and brought to pH 4.0 with dil. sodium hydroxide solution. The white solid so formed was filtered off, washed well with water and recrystallised from acetic acid, m.p. >355° C.

(Found: C, 67.02; H, 7.38; N, 8.06; $C_{10}H_{13}NO_2$. Requires: C, 67.02; H, 7.31; N, 7.82%).

c. 5,6-Cycloheptenyl-4-hydroxy-3-nitroα-pyridone

To a suspension of 5,6-cycloheptenyl-4-hydroxyα-pyridone (1.61g; 0.009 mole) in glacial acetic acid (10 ml) was added concentrated nitric acid (2.5 ml; d 1.42). The resulting clear solution was heated at 100° C till the exothermic reaction started, rapidly cooled and the nitro derivative precipitated by addition of water (50 ml). After filtration and recrystallisation from acetic acid; ethanol it had m.p. 233° –5° (d).

Found: C, 53.77; H, 5.42; N, 12.37; $C_{10}H_{12}N_2O_4$. Requires: C, 53.57; H, 5.39; N, 12.49%).

EXAMPLE 5 a. 3-Carboethoxy-5,7-dimethyl-4-hydroxy-5,6,7,8-tetrahydrocarbostyril

A solution of ethyl 2-amino-4,6-dimethyl cyclohex-1-ene-carboxylate (21.45 g; 0.109 mole) and diethyl malonate (17.5 g; 0.109 mole) was cyclised as described in Example 1a. The product on recrystallisation from ethanol had m.p. 264° C.

(Found: C, 63.34; H, 7.37; N, 5.19; $C_{14}H_{19}NO_4$. Requires: C, 63.38; H, 7.22; N, 5.28%).

b. 5,7-Dimethyl-4-hydroxy-5,6,7,8-tetrahydrocarbostyril

Hydrolysis of 3-carboethoxy-5,7-dimethyl-4-hydroxy-5,6,7,8-tetrahydrocarbostyril as described in Example 1b afforded the title compound. On recrystallisation from glacial acetic acid it had m.p. >300° C.

(Found: C, 68.63; H, 8.05; N, 7.20; $C_{11}H_{15}NO_2$. Requires: C, 68.37; H, 7.82; N, 7.25%).

c. 5,7-Dimethyl-4-hydroxy-3-nitro-5,6,7,8-tetrahydrocarbostyril

Nitration of 5,7-dimethyl-4-hydroxy-5,6,7,8-tetrahydrocarbostyril with concentrated nitric acid as described in Example 1c, gave the 3-nitro derivative, m.p. (acetic acid - ethanol) 235° –6° C (d).

(Found: C, 55.46; H, 5.88; N, 11.62; $C_{11}H_{14}N_2O_4$. Requires: C, 55.46; H, 5.92; N, 11.76%).

EXAMPLE 6 a. 3-Carboethoxy-4-hydroxy-6-methyl-5,6,7,8-tetrahydrocarbostyril

Condensation of ethyl 2-amino-5-methyl-cyclohex-1-ene-1-carboxylate (37 g; 0.202 mole) with diethyl malonate (32.4 g; 0.202 mole) at 110° C as described in Example 1 gave the title compound; m.p. (EtOH) 214° –216° C.

Found: C, 61.87; H, 6.85; N, 5.49; $C_{13}H_{17}NO_4$. Requires: C, 62.14; H, 6.82; N, 5.57%).

b. 4-Hydroxy-6-methyl-5,6,7,8-tetrahydrocarbostyril

Refluxing a suspension of 3-carboethoxy-4-hydroxy-6-methyl-5,6,7,8-tetrahydrocarbostyril (20 g; 0.08 mole) with 2N hydrochloric acid (300 ml) over 48 hrs. afforded the decarboethoxylated product isolated as in Example 1 m.p. (AcOH) >365° C.

(Found: C, 67.11; H, 7.46; N, 7.93; $C_{10}H_{13}NO_2$. Requires: C, 67.02; H, 7.31; N, 7.82%).

c. 4-Hydroxy-6-methyl-3-nitro-5,6,7,8-tetrahydrocarbostyril

Nitration of 4-hydroxy-6-methyl-5,6,7,8-tetrahydrocarbostyril as described in Example 1 gave the 3-nitro derivative as a yellow-orange crystalline solid, m.p. (EtOH) 243° – 244° C (d).

(Found: C, 53.52; H, 5.52; N, 12.30; $C_{10}H_{12}N_2O_4$ Requires; C, 53.57; H, 5.39; N, 12.49%).

EXAMPLE 7 a. 3-Carboethoxy-5,6-cyclooctenyl-4-hydroxy-α-pyridone

Using the procedure outlined in Example 1, ethyl 2-amino-cyclooct-1-ene-1-carboxylate (24 g) was converted into the α-pyridone, m.p. (EtOH) 232° – 234° C.

(Found: C, 63.43; H, 7.20; N, 5.24; $C_{14}H_{19}NO_4$. Requires: C, 63.38; H, 7.22; N, 5.28%).

b. 5,6-Cyclooctenyl-4-hydroxy-α-pyridone

Hydrolysis of 3-carboethoxy:5,6-cyclooctenyl-4-hydroxy-α-pyridone (4.1 g) are described gave the title product as a white crystalline solid, m.p. (AcOH) >300° C.

(Found: C, 68.27; H, 7.99; N, 7.27; $C_{11}H_{15}NO_2$. Requires: C, 68.37; H, 7.82; N, 7.25%).

c. 5,6-Cyclooctenyl 4-hydroxy-3-nitro-α-pyridone 5,6-Cyclooctenyl-4-hydroxy-α-pryidone (0.87 g) has been converted into its 3-nitro derivative as described in Example 1. After recrystallisation from ethanol it had m.p. 221° C (d).

(Found: C, 55.65; H, 5.98; N, 11.77; $C_{11}H_{14}N_2O_4$. Requires: C, 55.46; H, 5.92; N, 11.76%).

EXAMPLE 8 a. 1-Ethyl-4-hydroxy-5,6,7,8-tetrahydrocarbostyril

A solution of the ethyl and methyl esters (60:40 ratio) of 2-(N-ethyl-acetamido) cyclohex-1-ene-1-carboxylic acid (10 g; 0.043 mole) in dry dioxan (100 ml) was treated with sodium methoxide (2.54 g; 0.047 mole) and the mixture heated for 2 hrs. at 100° C. A white solid separated within a few minutes. After cooling the precipitate was filtered free of dioxan, taken up in a minimum of water and brought to pH 4 with concentrated hydrochloric acid. The product separated as a white solid which after filtration was recrystallised from glacial acetic acid, m.p. 355° –358° C (d).

(Found: C, 68.23; H, 7.88; N, 7.09; $C_{11}H_{15}NO_2$. Requires: C, 68.37; H, 7.82; N, 7.25%).

b. 1-Ethyl-4-hydroxy-3-nitro-5,6,7,8-tetrahydrocarbostyril

A suspension of 1-ethyl-4-hydroxy-5,6,7,8-tetrahydrocarbostyril (1.74 g; 0.009 mole) in glacial acetic acid (10 ml) was solubilised with concentrated nitric acid (2.5 ml; d 1.42) and the mixture heated for a few minutes at 100° C. After cooling and dilution with water a yellow crystalline solid separated. On recrystallisation from ethanol it had m.p. 152°– 154° C (d).

(Found: C, 55.39; H, 6.02; N, 11.76; $C_{11}H_{14}N_2O_4$. Requires: C, 55.46; H, 5.92; N, 11.76%).

EXAMPLE 9 a. 4-Hydroxy-1-n-propyl-5,6,7,8-tetrahydrocarbostyril

Cyclisation of a 60:40 mixture of the ethyl and methyl esters of 2-(N-n-propyl-acetamido) cyclohex-1-ene-1-carboxylic acid (34.82 g; 0.141 mole) as described in Example 8 afforded the title product as a white crystalline solid, m.p. (EtOH) 277° –278° C (Found: C, 69.23; H, 8.05; N, 6.74; $C_{12}H_{17}NO_2$. Requires: C, 69.54; H, 8.27; N, 6.76%).

b. 4-Hydroxy-3-nitro-1-n-propyl-5,6,7,8-tetrahydrocarbostyril

The 3-nitro derivative of 4-hydroxy-1-n-propyl-5,6,7,8-tetrahydrocarbostyril was prepared as in Example 8. It had m.p. (EtOH) 139° –141° C (Found: C, 57.02; H, 6.44; N, 11.23; $C_{12}H_{16}N_2O_4$. Requires: C, 57.13; H, 6.39; N, 11.10%).

EXAMPLE 10 a. 4-Hydroxy-1-isopropyl-5,6,7,8-tetrahydrocarbostyril

Cyclisation of a 60:40 mixture of the ethyl and methyl esters of 2-(N-isopropyl-acetamido)cyclohex-1-ene-1-carboxylic acid (14.16 g; 0.057 mole) with sodium methoxide (3.5 g; 0.064 mole) in dry dioxan (100 ml) over 6 hrs. at 100° C gave the title compound and after work-up as in Example 8. It had m.p. (EtOH) 304° – 307° C (d).

(Found: C, 69.51; H, 8.92; N, 6.36; $C_{12}H_{17}NO_2$. Requires C, 69.54; H, 8.27; N, 6.76%).

b. 4-Hydroxy-1-isopropyl-3-nitro-5,6,7,8-tetrahydrocarbostryil

Nitration of 4-hydxoxy-1-isopropyl-5,6,7,8-tetrahydrocarbostyril (1.86 g; 0.009 mole) with nitric acid in acetic acid as described in Example 8 afforded the 3-nitro derivative as a yellow crystalline solid, m.p. (EtOH) 171°– 173° C (Found: C, 56.84; H, 6.41; N, 11.16; $C_{12}H_{16}N_2O_4$. Requires: C, 57.13; H, 6.39; N, 11.10%).

EXAMPLE 11 a. 1-Ethyl-4-hydroxy-7-methyl-5,6,7,8-tetrahydrocarbostyril

The reaction of a 1:9 mixture of the methyl and ethyl esters of 2-(N-ethyl-acetamido)-4-methyl-cyclohex-1-ene-1-carboxylate (36.3 g; 0.144 mole) with dry sodium methoxide in dioxan as described in Example 8 gave the title product as a white crystalline solid; m.p. (EtOH) 335° – 338° C.

(Found: C, 69.33; H, 8.70; N, 7.21; $C_{12}H_{17}NO_2$. Requires: C, 69.54; H, 8.27; N, 6.76%).

b. 1-Ethyl-4-hydroxy-7-methyl-3-nitro-5,6,7,8-tetrahydrocarbostyril

Nitration of 1-ethyl-4-hydroxy-7-methyl-5,6,7,8-tetrahydrocarbostyril (1.86 g; 0.009 mole) in acetic acid (10 ml) as described in Example 8 yielded the 3-nitro derivative, m.p. (EtOH) 137° – 140° C (d).

(Found: C, 56.99; H, 6.57; N, 11.06; $C_{12}H_{16}N_2O_4$. Requires: C, 57.13; H, 6.39; N, 11.10%).

By the procedure of Example 1, the following compounds are prepared:

12. 7-ethyl-4-hydroxy-3-nitro-5,6,7,8-tetrahydrocarbostyril;
13. 6,7-diethyl-4-hydroxy-3-nitro-5,6,7,8-tetrahydrocarbostyril;
14. 6,7-dimethyl-4-hydroxy-3-nitro-5,6,7,8-tetrahydrocarbostyril.

BIOLOGICAL RESULTS

Some of the substituted 4-hydroxy-3-nitro-α-pyridones prepared in the previous examples were submitted for biological testing. The test system was the Rat Passive Cutaneous Anaphylaxis (PCA) test described below in (ii).

i. Serum containing heat labile homocytotropic antibody was raised in rats by a method similar to that used by Mota. (I. Mota Immunology 1964, 1, 681).

Male Wistar rats of 250–300g, were injected intraperitoneally with 0.5 ml of Bordatella pertussis vaccine (containing 4 × $10^{10}$ dead organism per ml) and subcutaneously with 0.5 ml of an emulsion of 100mg of ovalbumin in 2ml of saline and 3ml of incomplete Freunds' adjuvant. Rats were bled by cardiac puncture on day 18, the blood was pooled and separated and serum stored at −20° C and thawed only once before use.

ii. The P.C.A. test was similar to that described by Ovary and Bier (A. Ovary and O. E. Bier, Proc.Soc..Exp. Biol.Med.1952, 82, 584) and Goose and Blair (J. Goose and A. M. J. N. Blair, Immunology 1969, 16, 769).

0.1ml. of each of six twofold serial dilutions of the serum in 0.9% saline were injected intradermally into separate sites on the shaved dorsal surface of 250–350 g Wistar rats. 72 hours later the animals were challenged by i.v. injection of 0.3ml of 1% ovalbumin mixed with 0.1ml of a 5% solution of pontamine sky blue dye both in isotonic saline buffered with pH 7.2 Sorenson buffer (P.B.S.). The rats were killed after 20 minutes and the diameter of the blue wheals at the antibody injection sites were measured. The starting dilution of the serum was adjusted so that there was no response, after challenge, at the site of injection of the highest dilution and a maximum response at the lowest dilution. Typically, six twofold serial dilutions of the serum from ¼ to 1/128 were used.

Compounds were tested for their ability to reduce the diameter of the wheals at the injection sites of dilutions of antibody which on all the controls have less than maximum response. Amounts of the compounds were administered to rats each amount to a test group of six animals at a specified time prior to intravenous challenge with ovalbumin. The diameters of the blue wheals which developed on the test group of animals were compared with those on a control group of six animals treated in the same way as the test group, but which had not received the compound under test.

% Inhibition of P.C.A. = 100 (1 −a/b)

a = The mean of the sum of the diameters of the wheals produced in the test group of animals at those antibody sites where all the control group of animals gave less than maximum response.

b = The mean of the sum of diameters of the wheals produced in the control group of animals at those antibody sites where all the animals in the group gave less than the maximum response.

The compounds were administered either as a solution of the free nitro compound or as a solution or suspension in 1% methyl cellulose of the sodium salt.

BIOLOGICAL RESULTS

| | dose (mg/Kg) | Time (mins) | % inhibition of rat PCA response |
|---|---|---|---|
| Example 1. 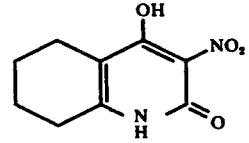 | 25<br>100<br>25<br>100 | 0<br>0<br>30<br>30 | 16<br>70<br>15<br>20 |
| Example 2. 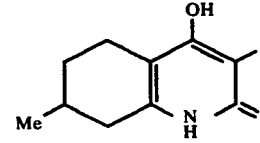 | 25<br>100<br>25<br>100 | 0<br>0<br>30<br>30 | 36<br>76<br>49<br>40 |
| Example 3. 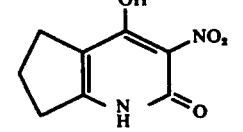 | 25<br>100<br>25<br>100 | 0<br>0<br>30<br>30 | 10<br>28<br>−20<br>6 |
| Example 4. 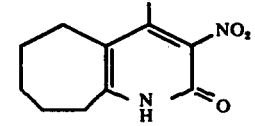 | 25<br>100<br>25<br>100 | 0<br>0<br>60<br>60 | −10<br>−3<br>1<br>27 |

BIOLOGICAL RESULTS-continued

| | dose (mg/Kg) | Time (mins) | % inhibition of rat PCA response |
|---|---|---|---|
| Example 5. 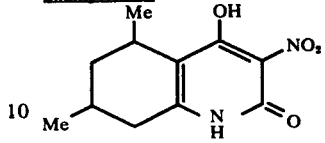 | 25<br>100<br>25<br>100 | 0<br>0<br>30<br>30 | 27<br>72<br>14<br>42 |
| Example 6. 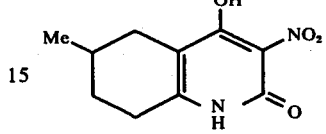 | 25<br>100<br>25<br>100 | 0<br>0<br>60<br>60 | 1<br>24<br>15<br>37 |
| Example 7. 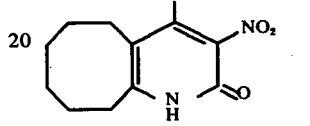 | 25<br>100<br>25<br>100 | 10<br>10<br>30<br>30 | 17<br>59<br>15<br>37 |
| Example 8. 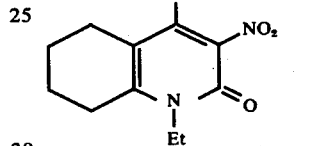 | 25<br>100<br>25<br>100 | 0<br>0<br>30<br>30 | −5<br>12<br>14<br>75 |
| Example 9. 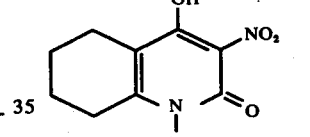 | 25<br>100<br>25<br>100 | 0<br>0<br>30<br>30 | −1<br>18<br>25<br>69 |
| Example 10. 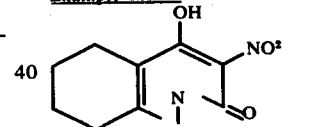 | 25<br>100<br>25<br>100 | 0<br>0<br>30<br>30 | 5<br>8<br>0<br>16 |
| Example 11. 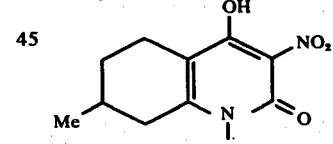 | 25<br>100<br>25<br>100 | 0<br>0<br>30<br>30 | 8<br>31<br>38<br>57 |

We claim:

1. The compound which is 4-hydroxy-7-methyl-3-nitro-5,6,7,8-tetrahydrocarbostyril.

2. The compound which is 5,7-dimethyl-4-hydroxy-3-nitro-5,6,7,8-tetrahydrocarbostyril.

3. The compound which is 7-ethyl-4-hydroxy-3-nitro-5,6,7,8-tetrahydrocarbostyril.

4. The compound which is 7-6,7-diethyl-4-hydroxy-3-nitro-5,6,7,8-tetrahydrocarbostyril.

5. The compound which is 6,7-dimethyl-4-hydroxy-3-nitro-5,6,7,8-tetrahydrocarbostyril.

* * * * *